United States Patent
Wada et al.

(10) Patent No.: US 9,149,800 B2
(45) Date of Patent: Oct. 6, 2015

(54) METHOD FOR PRODUCING RUTHENIUM CATALYST AND METHOD FOR PRODUCING ALKYL GROUP—OR ALKENYL GROUP-SUBSTITUTED COMPOUND USING RUTHENIUM CATALYST

(71) Applicant: KYOTO UNIVERSITY, Kyoto-shi, Kyoto (JP)

(72) Inventors: Kenji Wada, Kyoto (JP); Hiroki Miura, Kyoto (JP); Masahiro Nagao, Kyoto (JP); Saburo Hosokawa, Kyoto (JP); Masashi Inoue, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 14/375,681

(22) PCT Filed: Feb. 1, 2013

(86) PCT No.: PCT/JP2013/052379
§ 371 (c)(1),
(2) Date: Jul. 30, 2014

(87) PCT Pub. No.: WO2013/115378
PCT Pub. Date: Aug. 8, 2013

(65) Prior Publication Data
US 2015/0165433 A1    Jun. 18, 2015

(30) Foreign Application Priority Data

Feb. 2, 2012   (JP) ................. 2012-021025

(51) Int. Cl.
| | |
|---|---|
| *B01J 37/08* | (2006.01) |
| *B01J 31/26* | (2006.01) |
| *B01J 31/38* | (2006.01) |
| *B01J 23/46* | (2006.01) |
| *C07C 45/69* | (2006.01) |
| *C07C 45/70* | (2006.01) |
| *C07F 7/18* | (2006.01) |
| *C07D 333/22* | (2006.01) |
| *C07D 307/40* | (2006.01) |

(52) U.S. Cl.
CPC ............. *B01J 37/08* (2013.01); *B01J 23/462* (2013.01); *B01J 31/26* (2013.01); *B01J 31/38* (2013.01); *C07C 45/69* (2013.01); *C07C 45/70* (2013.01); *C07D 307/40* (2013.01); *C07D 333/22* (2013.01); *C07F 7/1892* (2013.01); *B01J 2231/44* (2013.01); *B01J 2531/005* (2013.01); *B01J 2531/007* (2013.01); *C07C 2102/10* (2013.01); *C07C 2103/94* (2013.01)

(58) Field of Classification Search
CPC ...................................................... B01J 37/08
USPC ............................................................ 549/70
See application file for complete search history.

(56) References Cited

FOREIGN PATENT DOCUMENTS

| | | |
|---|---|---|
| JP | 2010-184881 A | 8/2010 |
| JP | 2010-189313 A | 9/2010 |

OTHER PUBLICATIONS

Gao et al., *Angew. Chem. Int. Ed.*, 50: 6888-6892 (2011).
Jia et al., *Acc. Chem. Res.*, 34: 633-639 (2001).
Kakiuchi et al., *Acc. Chem. Res.*, 35: 826-834 (2002).
Kakiuchi et al., *Bull. Chem. Soc. Jpn.*, 68: 62-83 (1995).
Kakiuchi et al., *J. Am. Chem. Soc.*, 132: 17741-17750 (2010).
Kakiuchi et al., *Synthesis*, 19: 3013-3039 (2008).
Martinez et al., *Angew. Chem. Int. Ed.*, 45: 8232-8235 (2006).
Martinez et al., *Chem. Commun.*, 3855-3857 (2008).
Martinez et al., *J. Am. Chem. Soc.*, 131: 7887-7895 (2009).
Miura et al., *ChemCatChem*, 2(10): 1223-1225 (2010).
Murai et al., *Nature*, 366: 529-531 (1993).
Nevado et al., *Synthesis*, 2: 167-182 (2005).
Nishiumi et al., *ACS Catalysis*, 1753-1759 (2012).
Shimura et al., *ChemCatChem*, 4(12): 2062-2067 (2012).
Simon et al., *Organic Letters*, 12(13): 3038-3041 (2010).
Japanese Patent Office, International Search Report in International Patent Application No. PCT/JP2013/052379 (May 7, 2013).

*Primary Examiner* — Taofiq A Solola
(74) *Attorney, Agent, or Firm* — Leydig, Voit & Mayer, Ltd.

(57) ABSTRACT

This invention relates to a method for producing a ruthenium catalyst in which ruthenium supported on at least one metal oxide is pretreated with an aldehyde compound, a phosphorus compound, and a lower alcohol compound, and a method for producing alkyl- or alkenyl-substituted compound using the ruthenium catalyst.

12 Claims, No Drawings

METHOD FOR PRODUCING RUTHENIUM CATALYST AND METHOD FOR PRODUCING ALKYL GROUP—OR ALKENYL GROUP-SUBSTITUTED COMPOUND USING RUTHENIUM CATALYST

CROSS-REFERENCE TO RELATED APPLICATIONS

This patent application is the U.S. national phase of International Application No. PCT/JP2013/052379, filed Feb. 1, 2013, which claims the benefit of Japanese Patent Application No. 2012-021025, filed on Feb. 2, 2012, which are incorporated by reference in their entireties herein.

TECHNICAL FIELD

The present invention relates to a method for producing a ruthenium catalyst supported on at least one metal oxide, and a method for producing an alkyl- or alkenyl-substituted compound using a heterogeneous catalyst that is a ruthenium catalyst supported on at least one metal oxide.

BACKGROUND ART

A method for producing an alkyl- or alkenyl-substituted compound, an industrially important key compound, by an addition reaction to an unsaturated compound that involves carbon-carbon bond formation due to regioselective activation of a carbon-hydrogen bond is an excellent method with an atom efficiently of 100% that eliminates the need for prior activation of substrates, and that theoretically produces no by-products.

A method for producing such key compounds through the above route using a homogeneous complex catalyst containing metal such as ruthenium, palladium, or cobalt, is known (for example, Non-patent Literature 2 to 13). However, there are practical problems with the use of homogeneous complex catalysts, such as: 1) the catalyst production process is complicated, resulting in high environmental burden and high costs; 2) it is difficult to separate/recover and recycle the catalysts, which poses a problem of contamination of products by metals; and 3) in general, homogeneous complex catalysts are chemically and thermally unstable, and thus difficult to handle.

A production method that uses a solid catalyst is proposed, for example, in Patent Literature 1 and Non-patent Literature 1 to address the above problems. Although problems 1) to 3) described above, which are caused when homogeneous complex catalysts are used, can be solved by the methods of Patent Literature 1 and Non-patent Literature 1, there are problems such that the unsaturated compound that undergoes addition is limited to vinylsilane having at least one alkoxy group, and that the catalyst easily loses activity when recycled. For practical use in addition to such problems, catalytic activity must be further improved.

CITATION LIST

Patent Literature

PTL 1: JP2010-018488A

Non-Patent Literature

NPL 1: H. Miura, K. Wada, S. Hosokawa, M. Inoue, ChemCatChem 2010, 2, 1223-1225.

NPL 2: S. Murai, F. Kakiuchi, S. Sekine, Y. Tanaka, A. Kamatani, M. Sonoda, N. Chatani, Nature 1993, 366, 529-530.

NPL 3: C. G. Jia, T. Kitamura, Y. Fujiwara, Acc. Chem. Res. 2001, 34, 633-639.

NPL 4: C. Nevado, A. M. Echavarren, Synthesis 2005, 2, 167-182.

NPL 5: F. Kakiuchi, S. Murai, Acc. Chem. Res. 2002, 35, 826-834.

NPL 6: F. Kakiuchi, T. Kochi, Synthesis 2008, 19, 3013-3039.

NPL 7: F. Kakiuchi, S. Sekine, Y. Tanaka, A. Kamatani, M. Sonoda, N. Chatani, S. Murai, Bull. Chem. Soc. Jpn. 1995, 68, 62-83.

NPL 8: R. Martinez, R. Chevalier, S. Darses, J.-P. Genet, Angew. Chem. Int. Ed. 2006, 45, 8232-8235.

NPL 9: R. Martinez, J.-P. Genet, S. Darses, Chem. Commun. 2008, 3855-3857.

NPL 10: R. Martinez, M.-O. Simon, R. Chevalier, C. Pautigny, J.-P. Genet, S. Darses, J. Am. Chem. Soc. 2009, 131, 7887-7895.

NPL 11: M.-O. Simon, J.-P. Genet, S. Darses, Org. Lett. 2010, 12, 3038-3041.

NPL 12: F. Kakiuchi, T. Kochi, E. Mizushima, S. Murai, J. Am. Chem. Soc. 2010, 132, 17741-17750.

NPL 13: K. Gao, N. Yoshikai, Angew. Chem. Int. Ed. 2011, 50, 6888-6892.

SUMMARY OF INVENTION

Technical Problem

An object of the present invention is to provide a method for producing a ruthenium catalyst supported on at least one metal oxide, the catalyst being applicable to a remarkably wide range of raw materials, having higher activity than hitherto known catalysts, and being capable of being recycled without decreasing catalytic activity.

Another object of the present invention is to provide a method for producing an alkyl- or alkenyl-substituted compound with higher efficiency and small burden on the environment or the like, wherein the use of the metal oxide-supported ruthenium catalyst allows a reaction to proceed in raw materials in which the reaction does not proceed with hitherto known ruthenium-based solid catalysts.

Solution to Problem

The present inventors conducted extensive research to achieve the above objects, and found that an alkyl- or alkenyl-substituted compound can be obtained by subjecting a specific ruthenium catalyst supported on at least one metal oxide to pretreatment under specific conditions. The present invention has been accomplished based on this finding.

Specifically, the present invention relates to the following production methods.

Item 1.

A method for producing a ruthenium catalyst, the method comprising mixing ruthenium supported on at least one metal oxide selected from the group consisting of rare-earth metal oxides, zirconium oxide, and composite oxides containing one or more rare-earth metal oxides and/or zirconium oxide, an aldehyde compound, a phosphorus compound, and a lower alcohol compound, and heating the mixture.

Item 2.
 The method for producing a ruthenium catalyst according to Item 1, wherein the aldehyde compound is at least one member selected from the group consisting of formaldehyde, 1,3,5-trioxane, paraformaldehyde, glyoxal, methylglyoxal, malonaldehyde, acetaldehyde, and propionaldehyde.
Item 3.
 The method for producing a ruthenium catalyst according to Item 1, wherein the aldehyde compound is formaldehyde.
Item 4.
 The method for producing a ruthenium catalyst according to Item 1, wherein the phosphorus compound is at least one member selected from the group consisting of phosphines, phosphites, and phosphine oxides.
Item 5.
 The method for producing a ruthenium catalyst according to Item 1, wherein the phosphorus compound is triphenylphosphine.
Item 6.
 The method for producing a ruthenium catalyst according to Item 1, wherein the lower alcohol compound is at least one member selected from the group consisting of lower alcohols, lower alkylene glycols, and lower alkoxy-lower alcohols.
Item 7.
 The method for producing a ruthenium catalyst according to Item 1, wherein the lower alcohol compound is 2-methoxyethanol.
Item 8.
 The method for producing a ruthenium catalyst according to any one of Items 1 to 7, wherein the heating temperature is 40 to 200° C.
Item 9.
 A method for producing compound (3), comprising:
 reacting compound (1) having a partial structure of formula (1-1) with a compound represented by formula (2) in the presence of the metal oxide-supported ruthenium catalyst obtained by the method according to any one of Items 1 to 8 to obtain compound (3) having a partial structure of formula (3-1),

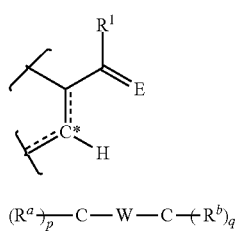

(1-1)

<br>

$(R^a)_p$—C—W—C—$(R^b)_q$ (2)

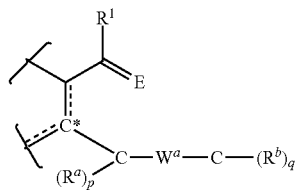

(3-1)

wherein
 $R^1$ is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-Si($R^{1'}$)$_m$($OR^{2'}$)$_{3-m}$ (in formula (a), m is an integer of 0 to 3, and $R^1$ and $R^{2'}$ may be the same or different and each is lower alkyl or an aromatic ring);
 E is an oxygen atom;
 $R^a$ and $R^b$ may be the same or different and each is a hydrogen atom, a straight or branched lower alkyl, lower alkoxy, or lower alkyl-carbonyl group that may be substituted with one or more halogen atoms, lower alkenyl, lower alkynyl, carbamoyl, an unsaturated heterocyclic ring, an aromatic ring, nitro, amino, amido, an ester group, carboxyl, hydroxyl, cyano, a halogen atom, or a group represented by formula (a):-Si($R^{1'}$)$_m$($OR^{2'}$)$_{3-m}$ (in formula (a), m, $R^{1'}$, and $R^{2'}$ are the same as in the above formula);
 $R^a$ and $R^b$ may be combined to form a bicyclo ring;
 p and q are each 1 or 2, p and q are each 2 when W is a double bond, and p and q are each 1 when W is a triple bond;
 C* is sp² carbon;
 one of two bonds of C* represented by a solid line and a dotted line is a double bond, and the other is a single bond;
 W is a double bond or a triple bond; and
 $W^a$ is a single bond or a double bond.
Item 10.
 The method according to Item 9, comprising:
 reacting a compound represented by formula (1a) with a compound represented by formula (2) in the presence of the ruthenium catalyst to obtain a compound represented by formula (3a),

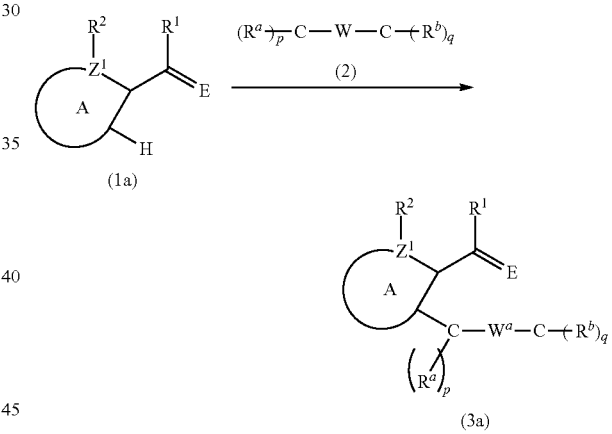

wherein
 E is an oxygen atom;
 $R^1$ and $R^2$ may be the same or different and each is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-Si($R^{1'}$)$_m$($OR^{2'}$)$_{3-m}$ (in formula (a), m is an integer of 0 to 3, and $R^{1'}$ and $R^{2'}$ may be the same or different and each is lower alkyl or an aromatic ring), or
 $R^1$ and $R^2$ are bonded to each other via or not via one or more heteroatoms to form a 5- to 10-membered unsaturated hydrocarbon ring, a 5- to 10-membered unsaturated heterocyclic ring, or a 5- to 10-membered aromatic ring, wherein the formed ring may have at least one substituent selected from the group consisting of a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, and a halogen atom;

Ring A is bonded to each other via or not via one or more heteroatoms to form a 5- to 10-membered unsaturated hydrocarbon ring, a 5- to 10-membered unsaturated heterocyclic ring, or a 5- to 10-membered aromatic ring that may have one or more heteroatoms, wherein the formed ring may have at least one substituent selected from the group consisting of a straight or branched lower alkyl, lower alkoxy, or lower alkyl-carbonyl group that may be substituted with one or more halogen atoms, carbamoyl, an unsaturated heterocyclic ring, an aromatic ring, nitro, amino, amido, an ester group, carboxyl, hydroxyl, cyano, a halogen atom, and a group represented by formula (a):-Si$(R^{1'})_m(OR^{2'})_{3-m}$ (in formula (a), m, $R^{1'}$, and $R^{2'}$ are the same as in the above formula);

$Z^1$ is a carbon atom or a heteroatom, with the proviso that when $Z^1$ is a heteroatom other than a nitrogen atom, $R^2$ is not substituted, and when $Z^1$ is a nitrogen atom, $R^2$ may be substituted;

$R^a$ and $R^b$ may be the same or different and each is a hydrogen atom, a straight or branched lower alkyl, lower alkoxy, or lower alkyl-carbonyl group that may be substituted with one or more halogen atoms, lower alkenyl, lower alkynyl, carbamoyl, an unsaturated heterocyclic ring, an aromatic ring, nitro, amino, amido, an ester group, carboxyl, hydroxyl, cyano, a halogen atom, or a group represented by formula (a):-Si$(R^{1'})_m(OR^{2'})_{3-m}$ (in formula (a), m, $R^{1'}$, and $R^{2'}$ are the same as in the above formula);

$R^a$ and $R^b$ may be combined to form a bicyclo ring;

p and q are each 1 or 2, p and q are each 2 when W is a double bond, and p and q are each 1 when W is a triple bond;

W is a double bond or a triple bond; and $W^a$ is a single bond or a double bond.

Item 11.

The method according to Item 9, comprising:

reacting a compound represented by formula (1b) with a compound represented by formula (2) in the presence of the ruthenium catalyst to obtain a compound represented by formula (3b),

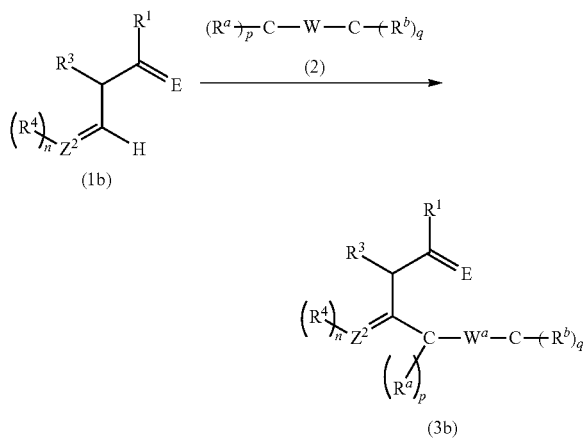

wherein
 E is an oxygen atom;
 $R^1$ is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-Si$(R^{1'})_m(OR^{2'})_{3-m}$ (in formula (a), m is an integer of 0 to 3, $R^{1'}$ and $R^{2'}$ may be the same or different and each is lower alkyl or an aromatic ring), $R^3$ is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-Si$(R^{1'})_m(OR^{2'})_{3-m}$ (in formula (a), m, $R^{1'}$, and $R^{2'}$ are the same as in the above formula), or $R^1$ and $R^3$ are bonded to each other via or not via one or more heteroatoms to form a 5- to 10-membered saturated hydrocarbon ring, a 5- to 10-membered unsaturated heterocyclic ring, or a 5- to 10-membered aromatic ring, wherein the formed ring may have at least one substituent selected from the group consisting of a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, and a halogen atom;

$R^4$ is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-Si$(R^{1'})_m(OR^{2'})_{3-m}$ (in formula (a), m, $R^{1'}$, and $R^{2'}$ are the same as in the above formula);

$Z^2$ is a carbon atom or a nitrogen atom;

n is 1 or 2, n is 2 and $R^4$s may be the same or different when $Z^2$ is a carbon atom, and n is 1 when $Z^2$ is a nitrogen atom;

$R^a$ and $R^b$ may be the same or different and each is a hydrogen atom, a straight or branched lower alkyl, lower alkoxy, or lower alkyl-carbonyl group that may be substituted with one or more halogen atoms, lower alkenyl, lower alkynyl, carbamoyl, an unsaturated heterocyclic ring, an aromatic ring, nitro, amino, amido, an ester group, carboxyl, hydroxyl, cyano, a halogen atom, or a group represented by formula (a):-Si$(R^{1'})_m(OR^{2'})_{3-m}$ (in formula (a), m, $R^{1'}$, and $R^{2'}$ are the same as in the above formula);

$R^a$ and $R^b$ may be combined to form a bicyclo ring;

p and q are each 1 or 2, p and q are each 2 when W is a double bond, and p and q are each 1 when W is a triple bond;

W is a double bond or a triple bond; and $W^a$ is a single bond or a double bond.

Item 12.

The method according to Item 9, comprising:

reacting a compound represented by formula (1c) with a compound represented by formula (2) in the presence of the ruthenium catalyst to obtain a compound represented by formula (3c),

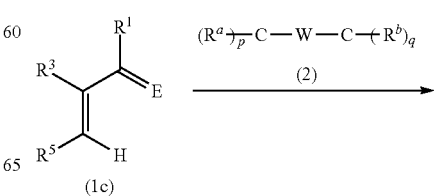

-continued

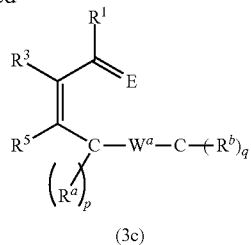

(3c)

wherein

E is an oxygen atom;

$R^1$ is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-Si$(R^{1'})_m$ $(OR^{2'})_{3-m}$ (in formula (a), m is an integer of 0 to 3, $R^{1'}$ and $R^{2'}$ may be the same or different and each is lower alkyl or an aromatic ring), $R^3$ is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-Si$(R^{1'})_m$ $(OR^{2'})_{3-m}$ (in formula (a), m, $R^{1'}$, and $R^{2'}$ are the same as in the above formula), or $R^1$ and $R^3$ are bonded to each other via or not via one or more heteroatoms to form a 5- to 10-membered saturated hydrocarbon ring, a 5- to 10-membered unsaturated heterocyclic ring, or a 5- to 10-membered aromatic ring, wherein the formed ring may have at least one substituent selected from the group consisting of a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, and a halogen atom;

$R^5$ is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-Si$(R^{1'})_m$ $(OR^{2'})_{3-m}$ (in formula (a), m, $R^{1'}$, and $R^{2'}$ are the same as in the above formula);

$R^a$ and $R^b$ may be the same or different and each is a hydrogen atom, a straight or branched lower alkyl, lower alkoxy, or lower alkyl-carbonyl group that may be substituted with one or more halogen atoms, lower alkenyl, lower alkynyl, carbamoyl, an unsaturated heterocyclic ring, an aromatic ring, nitro, amino, amido, an ester group, carboxyl, hydroxyl, cyano, a halogen atom, or a group represented by formula (a):-Si$(e)_m(OR^{2'})_{3-m}$ (in formula (a), m, $R^{1'}$, and $R^{2'}$ are the same as in the above formula);

$R^a$ and $R^b$ may be combined to form a bicyclo ring;

p and q are each 1 or 2, p and q are each 2 when W is a double bond, and p and q are each 1 when W is a triple bond;

W is a double bond or a triple bond; and $W^a$ is a single bond or a double bond.

Advantageous Effects of Invention

According to the present invention, a high-performance ruthenium catalyst having excellent environmentally friendly properties, such as reusability and suppression of metal leaching, can be produced.

In addition, the ruthenium catalyst is applicable to a wider range of raw materials compared to hitherto known ruthenium-based solid catalysts, and allows for the production of a more efficient, economical, and environmentally friendly alkyl- or alkenyl-substituted compound.

Further, with the ruthenium solid catalyst of the present invention, an optimum catalytically active species for the target reaction can be generated as desired by performing the reaction or pretreatment under appropriate conditions. Thus, the ruthenium-based solid catalyst obtained by the production method of the present invention can be applied to a wider range of reactions, including synthesis reactions with a high degree of difficulty that cannot be performed with hitherto known solid catalysts, and is expected to find application in metal oxide catalysts with significantly excellent environmental burden-, resource burden-, and energy burden-minimizing properties.

DESCRIPTION OF EMBODIMENTS

1. Method for Producing a Ruthenium Catalyst Supported on at Least One Metal Oxide The present invention relates to a method for producing a ruthenium catalyst supported on at least one metal oxide. Examples of the metal oxide (composite oxide) on which ruthenium is supported include rare-earth metal oxides, zirconium oxide, and composite oxides containing one or more rare-earth metal oxides and/or zirconium oxide, from the viewpoint, for example, that they commonly have high mechanical strength and thus can avoid disadvantages such as loss and contamination in a product due to catalyst attrition, powdering, or the like, when used for catalysts; that a catalyst with high activity can be easily prepared; that reactivation of a catalyst after use by calcination is easy; that they have high thermal and chemical stability; and that other by-products are not produced. Examples of rare-earth metal oxides include cerium oxide, praseodymium oxide, terbium oxide, ytterbium oxide, yttrium oxide, and the like. These metal oxides may be used singly, or in a combination of two or more. Of these metal oxides, zirconium oxide, cerium oxide, or a composite oxide containing one or both of them is preferable from the viewpoint of availability, price, catalytic activity, etc.

The metal oxide (one or more rare-earth metal oxides and/or zirconium oxide) may also be a composite oxide of the metal oxide and another or other metal oxides. Here, "composite oxides containing one or more rare-earth metal oxides and/or zirconium oxide" means composites of one or more rare-earth metal oxides and/or zirconium oxide and another or other metal oxides. Examples of metal oxides other than rare-earth metal oxides and/or zirconium oxide include titanium oxide, vanadium oxide, manganese oxide, iron oxide, cobalt oxide, nickel oxide, copper oxide, and the like.

In the case where the composite oxide is used, the content of the metal oxide(s) other than rare-earth metal oxide(s) and/or zirconium oxide is not particularly limited as long as the catalyst functions as a catalyst in production of the below-described compound (3). The content of the metal oxide(s) other than rare-earth metal oxide(s) and/or zirconium oxide in the composite oxide is, for example, preferably 50% by mass or less, more preferably 20% by mass or less, and even more preferably 10% by mass or less.

The metal oxide or composite oxide is obtained by using a salt of the metal, such as nitrate, oxynitrate, carbonate, oxalate, or acetate, as its precursor, and calcining it in air after hydrolysis.

A method for producing ruthenium supported on the metal oxide (composite oxide) is not particularly limited. For example, the metal oxide (composite oxide)-supported ruthenium is obtained by dissolving the below-described ruthenium precursor in a solvent and impregnating the metal oxide (composite oxide) in the solution, followed by calcination. Examples of the ruthenium precursor include $Ru_3(CO)_{12}$, $[RuCl_2(CO)_3]_2$, tetrachlorobis(p-cymene)diruthenium $([RuCl_2(p\text{-cymene})])_2)$, $RuCl_3 \cdot nH_2O$, (cyclooctadiene)(cyclooctatriene)ruthenium(0) complex (Ru(cod)(cot)), tris(acetylacetonate)ruthenium, ruthenium iodide, and the like. Examples of the solvent for dissolving the ruthenium precursor include ether-based solvents, such as tetrahydrofuran (THF); alcohol-based solvents, such as methanol; chlorine-based solvents, such as chloroform; and the like.

The calcination temperature after impregnating the metal oxide (composite oxide) in a solution of the ruthenium precursor is preferably about 200 to about 700° C., and more preferably about 300 to about 500° C.

The proportion of supported ruthenium in the metal oxide-supported ruthenium is about 0.005 to about 20% by mass, preferably about 0.01 to about 20% by mass, more preferably about 0.1 to about 5% by mass, and even more preferably about 0.5 to about 2% by mass. Setting the proportion of supported ruthenium to about 0.005% by mass or more can reduce the amount of a solid catalyst required for a reaction, thus lowering the catalyst cost. Additionally, setting the proportion of supported ruthenium to 20% by mass or less allows ruthenium species highly dispersed at the atomic level to be formed on the surface of a catalyst.

The ruthenium catalyst of the present invention is produced by mixing the metal oxide-supported ruthenium with an aldehyde compound, a phosphorus compound, and a lower alcohol compound, and heating the mixture.

Examples of the aldehyde compound include formaldehyde, 1,3,5-trioxane, paraformaldehyde, glyoxal, methylglyoxal, malonaldehyde, acetaldehyde, propionaldehyde, and the like. Of these, formaldehyde is preferable from the viewpoint that catalytic activity can be exhibited on a wide range of substrates represented by the below-described formulae (1a) to (1c) and formula (2); that the function can be exhibited with addition in a small amount; and the like. The formaldehyde may be used as a formalin solution (formaldehyde aqueous solution). When the formaldehyde is used as a formalin solution, the concentration of formaldehyde is preferably about 5 to about 50% by mass, and more preferably about 30 to about 40% by mass.

The amount of the aldehyde compound to be used is preferably about 1 to about 100 parts by mass, more preferably about 10 to about 50 parts by mass, and even more preferably about 20 to about 30 parts by mass, per part by mass of ruthenium in the metal oxide-supported ruthenium. Setting the content of the aldehyde compound to 1 part by mass or more is preferable from the viewpoint that a ruthenium catalyst having stably high catalytic activity on a wide range of substrates represented by the below-described formulae (1a) to (1c) and formula (2) can be reliably produced. Additionally, setting the content of the aldehyde compound to 100 parts by mass or less is preferable, for example, from the viewpoint that metal leaching is suppressed and that the amount of the aldehyde compound to be used can be reduced.

The phosphorus compound is mixed from the viewpoint that a catalyst capable of improving the yield of the desired compound can be obtained since the phosphorus compound has the effect of promoting reduction from the ruthenium oxo species to the low-valent ruthenium species, and the mechanism in which the phosphorus compound coordinates with the ruthenium species on the surface of the catalyst to change the electron state of the ruthenium species and appropriately controls the state of coordination of a substrate and a product to the ruthenium species.

Specific examples of the phosphorus compound include phosphines, phosphites, phosphine oxides, and the like. Specific examples of phosphines include triphenylphosphine ($PPh_3$), tri-p-tolylphosphine ($P(p\text{-tolyl})_3$), tris(4-fluorophenyl)phosphine ($P(p\text{-F}-C_6H_4)_3$), tris(4-trifluoromethylphenyl)phosphine ($P(p\text{-CF}_3-C_6H_4)_3$), trimethylphosphine, triethylphosphine, and the like. Specific examples of phosphites include trimethyl phosphite, triethyl phosphite, and the like. Specific examples of phosphine oxides include triphenylphosphine oxide ($POPh_3$), tri-p-tolylphosphine oxide ($PO(p\text{-tolyl})_3$), tris(4-fluorophenyl)phosphine oxide ($PO(p\text{-F}-C_6H_4)_3$), tris(4-trifluoromethylphenyl)phosphine oxide ($PO(p\text{-CF}_3-C_6H_4)_3$), trimethylphosphine oxide, and triethylphosphine oxide. Of these, $PPh_3$ is more preferable from the viewpoint that a catalyst that can improve the yield of the desired compound is obtained.

The amount of the phosphorus compound to be used is preferably about 0.1 to about 20 mol, more preferably about 1 to about 6 mol, and even more preferably about 3 to about 5 mol, per mol of ruthenium in the metal oxide-supported ruthenium. Setting the amount of the phosphorus compound to 1 mol or more attains the effect of allowing a reaction to proceed smoothly and selectively producing only the desired product in a high yield under mild conditions. Additionally, setting the amount of the phosphorus compound to 20 mol or less attains the effect of efficiently using the phosphorus compound without lowering the yield of the product.

Examples of the lower alcohol compound include lower alcohols having 1 to 6 carbon atoms, preferably 1 to 4 carbon atoms, and more preferably 1 to 3 carbon atoms, lower alkoxy-lower alcohols having 3 to 6 carbon atoms, preferably 3 to 5 carbon atoms, and more preferably 3 to 4 carbon atoms, and lower alkylene glycols having 2 to 4 carbon atoms and preferably 2 to 3 carbon atoms. The lower alcohol compound is preferably lower alkoxy-lower alcohol. Specific examples of lower alkoxy-lower alcohols include 2-methoxyethanol, 2-ethoxyethanol, 3-methoxypropanol, 2-methoxy-1-propanol, 3-ethoxypropanol, and 2-ethoxy-1-propanol. Specific examples of lower alcohols include methanol, ethanol, n-propanol, isopropanol, n-butanol, pentanol, and hexanol. Alkylene glycol, ethylene glycol, propylene glycol, butylene glycol, and the like can be mentioned. Of these, 2-methoxyethanol is more preferable from the viewpoint, for example, that a catalyst exhibiting catalytic activity on a wide range of substrates represented by the below-described formulae (1a) to (1c) can be obtained, and that 2-methoxyethanol has an appropriate boiling point.

After the metal oxide-supported ruthenium, the aldehyde compound, the phosphorus compound, and the lower alcohol compound are mixed, the mixture is heated. The heating temperature is preferably about 40 to about 200° C., more preferably about 80 to about 170° C., and even more preferably about 120 to about 150° C. Setting the heating temperature to 40° C. or more attains the effect of shortening the time required for pretreatment of a catalyst. Additionally, by setting the heating temperature to 200° C. or less, the loss of components having relatively low boiling points can be inhibited, thus enabling a reduction in the amount of additives required for the pretreatment. A highly active ruthenium catalyst can be obtained by performing such heat treatment.

The step of mixing the metal oxide-supported ruthenium, the aldehyde compound, the phosphorus compound, and the lower alcohol compound and heating the mixture is preferably performed under an inert gas atmosphere. Examples of inert gases include argon, nitrogen, helium, and the like.

After the heating, the volatile components (aldehyde compound and lower alcohol compound) are evaporated, thereby producing a ruthenium catalyst. As a method for evaporating the volatile components, a known method is usable.

The thus-obtained metal oxide-supported ruthenium catalyst can be recycled by separating and recovering the catalyst after the production of the below-described compound (3) (and, if necessary, washing it), followed by mixing the catalyst with an aldehyde compound, a phosphorus compound, and a lower alcohol compound, and heating the mixture.

The washing agent used for washing is not particularly limited. Examples thereof include THF, diethyl ether, methanol, ethanol, water, hexane, petroleum ether, mixtures thereof, and the like.

As the aldehyde compound, the phosphorus compound, and the lower alcohol compound, those mentioned above are usable. As the heating temperature, the heating temperature mentioned above can be employed.

2. Method for Producing Compound (3)

The present invention also relates to a method for producing compound (3), the method comprising reacting the below-described compound (1) with the below-described compound (2) in the presence of a ruthenium catalyst supported on at least one metal oxide obtained through the step of mixing ruthenium supported on at least one metal oxide, an aldehyde compound, a phosphorus compound, and a lower alcohol compound, and heating the mixture.

Compound (1) has a partial structure of formula (1-1) below, and more specifically encompasses a compound of formula (1a), a compound of formula (1b), and a compound of formula (1c).

Compound (3) has a partial structure of formula (3-1) below, and more specifically encompasses a compound of formula (3a), a compound of formula (3b), and a compound of formula (3c).

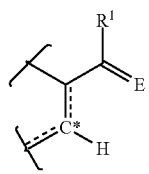

(1-1)

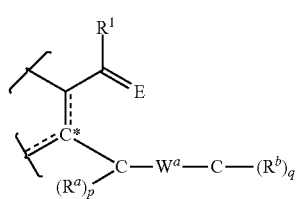

(3-1)

wherein $R^1$, E, $R^a$, $R^b$, $W^a$, p, and q are as defined above, C* is $sp^2$ carbon, one of two bonds of C* represented by a solid line and a dotted line is a double bond, and the other is a single bond.

As the metal oxide-supported ruthenium catalyst, a ruthenium catalyst produced by the method described above in "1. Method for producing a ruthenium catalyst supported on at least one metal oxide" is usable.

Compound (1), which is a substrate, may be a compound in which carbon bonded to a hydrogen atom that reacts with the below-described compound (2) is $sp^2$ carbon, i.e., a compound having carbon involved in a double bond. As Compound (1), a compound represented by formula (1a):

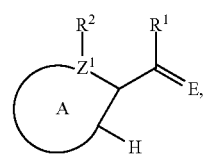

(1a)

formula (1b):

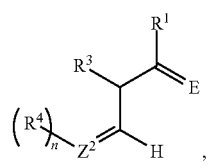

(1b)

or formula (1c):

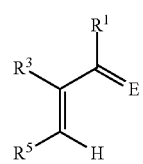

(1c)

wherein $R^1$, $R^2$, $R^3$, $R^4$, $R^5$, $Z^1$, $Z^2$, E, n, and ring A are as defined above, is used.

In formula (1a), regarding the hydrogen atom that reacts with compound (2), the carbon-hydrogen bond is activated by the metal oxide-supported ruthenium catalyst.

E is an oxygen atom from the viewpoint of allowing the ruthenium species on the catalyst to coordinate thereto to thereby place the ruthenium species in the vicinity of the C—H bond at the ortho position, resulting in the selective activity.

$R^1$ and $R^2$ may be the same or different and each is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-Si($R^{1'}$)$_m$(O$R^{2'}$)$_{3-m}$ (in formula (a), m is an integer of 0 to 3, $R^{1'}$ and $R^{2'}$ may be the same or different and each is lower alkyl or an aromatic ring).

In the present specification, examples of the straight or branched lower alkyl group that may be substituted with one or more halogen atoms include straight or branched lower alkyl groups that have about 1 to about 4 carbon atoms and that may be substituted with one or more halogen atoms, such as methyl, ethyl, n-propyl, iso-propyl, n-butyl, iso-butyl, sec-butyl, tert-butyl, trifluoromethyl, trichloromethyl, chloromethyl, bromomethyl, fluoromethyl, iodomethyl, difluoromethyl, dibromomethyl, dichloromethyl, 2-chloroethyl, 2,2,2- trifluoroethyl, 2,2,2-trichloroethyl, 3-chloropropyl, 2,3-dichloropropyl, 4,4,4-trichlorobutyl, and 4-fluorobutyl.

Examples of the straight or branched lower alkoxy group that may be substituted with one or more halogen atoms include straight or branched lower alkoxy groups that have about 1 to about 4 carbon atoms and that may be substituted with one or more halogen atoms, such as methoxy, ethoxy, n-propoxy, iso-propoxy, n-butoxy, iso-butoxy, sec-butoxy, tert-butoxy, trifluoromethoxy, trichloromethoxy, chloromethoxy, bromomethoxy, fluoromethoxy, iodomethoxy, difluoromethoxy, dibromomethoxy, dichloromethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, and 4-fluorobutoxy.

In the present specification, examples of the straight or branched lower alkyl-carbonyl group that may be substituted with one or more halogen atoms include carbonyl having a straight or branched lower alkyl group that has about 1 to about 4 carbon atoms and that may be substituted with one or more halogen atoms, such as methylcarbonyl, ethylcarbonyl, n-propylcarbonyl, iso-propylcarbonyl, n-butylcarbonyl, iso-butylcarbonyl, sec-butylcarbonyl, tert-butylcarbonyl, trifluoromethylcarbonyl, trichloromethylcarbonyl, chloromethylcarbonyl, bromomethylcarbonyl, fluoromethylcarbonyl, iodomethylcarbonyl, di fluoromethylcarbonyl, dibromomethylcarbonyl, dichloromethylcarbonyl, 2-chloroethylcarbonyl, 2,2,2-trifluoroethylcarbonyl, 2,2,2-trichloroethylcarbonyl, 3-chloropropylcarbonyl, 2,3-dichloropropylcarbonyl, 4,4,4-trichlorobutylcarbonyl, and 4-fluorobutylcarbonyl.

In the present specification, examples of amino include those represented by formulae: —NH$_2$, —NHR$^{3'}$, and —NR$^{3'}_2$ (wherein R$^{3'}$ is lower alkyl, and when the number of R$^{3'}$ is 2, i.e., in the case of —NR$^{3'}_2$, the lower alkyl groups may be the same or different). Specific examples of lower alkyl of R$^{3'}$ in the formulae include those exemplified in the explanation of the aforementioned lower alkyl group.

In the present specification, the unsaturated hydrocarbon ring may be monocyclic or polycyclic. Examples thereof include 5- to 10-membered unsaturated hydrocarbon rings and preferably 5- to 6-membered unsaturated hydrocarbon rings. Specific examples thereof include the following rings.

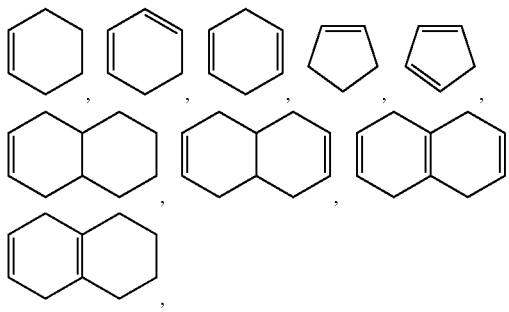

In the present specification, the unsaturated heterocyclic ring may be monocyclic or polycyclic. Examples thereof include 5- to 10-membered unsaturated heterocyclic rings, and preferably 5- to 6-membered unsaturated heterocyclic rings. Specific examples thereof include pyridine ring, pyrrole ring, oxazole ring, isoxazole ring, thiazole ring, isothiazole ring, furazan ring, imidazole ring, pyrazole ring, pyrazine ring, pyrimidine ring, pyridazine ring, dihydrooxazole ring, thiophene ring, furan ring, pyrazole ring, and the like.

In the present specification, the aromatic ring may be monocyclic or polycyclic. Examples thereof include 5- to 14-membered aromatic rings. Specific examples thereof include benzene ring, naphthalene ring, phenanthrene ring, and the like.

In the present specification, carbamoyl is —CONH$_2$.

In the present specification, examples of amido include those represented by formulae: —CONHR$^{3'}$ and —CONR$^{3'}_2$ (wherein R$^{3'}$ is lower alkyl, and when the number of R$^{3'}$ is 2, i.e., in the case of —NR$^{3'}_2$, the lower alkyl groups (R$^{3'}$) may be the same or different). Specific examples of lower alkyl of R$^{3'}$ in the formulae include those exemplified in the explanation of the aforementioned lower alkyl group.

In the present specification, examples of the ester group include those represented by formula: —COOR$^{3'}$ (wherein R$^{3'}$ is lower alkyl or aralkyl such as benzyl or phenethyl). Specific examples of lower alkyl of R$^{3'}$ in the formula include those exemplified in the explanation of the aforementioned lower alkyl group.

In the present specification, examples of the halogen atom include fluorine, chlorine, bromine, and iodine.

R$^{1'}$ and R$^{2'}$ in the group represented by formula (a):-Si(R$^{1'}$)$_m$(OR$^{3'}$)$_{3-m}$ may be the same or different and each is lower alkyl or an aromatic ring. Specific examples of lower alkyl and aromatic ring include those described above. Specific examples of the group represented by formula (a) include trimethylsilyl, dimethylphenylsilyl, trimethoxysilyl, dimethylethoxysilyl, and the like.

In addition, R$^1$ and R$^2$ may be bonded to each other via or not via one or more heteroatoms to form an optionally substituted unsaturated hydrocarbon ring, an optionally substituted unsaturated heterocyclic ring, or an optionally substituted aromatic ring.

The unsaturated hydrocarbon ring, the unsaturated heterocyclic ring, or the aromatic ring is preferably a 5- to 10-membered ring and more preferably 5- to 6-membered ring. The unsaturated hydrocarbon ring, the unsaturated heterocyclic ring, or the aromatic ring may be monocyclic or polycyclic. Examples of the unsaturated hydrocarbon ring, the unsaturated heterocyclic ring, and the aromatic ring include unsaturated hydrocarbon rings, such as cyclopentene and cyclohexene; unsaturated heterocyclic rings such as pyridine ring, pyrrole ring, oxazole ring, isoxazole ring, thiazole ring, isothiazole ring, furazan ring, imidazole ring, pyrazole ring, pyrazine ring, pyrimidine ring, pyridazine ring, dihydrooxazole ring, thiophene ring, furan ring, and pyrazole ring; aromatic rings, such as benzene ring, naphthalene ring, and phenanthrene ring; and the like. Two or more of these rings may be fused to form a polycyclic ring.

The unsaturated hydrocarbon ring, the unsaturated heterocyclic ring, or the aromatic ring may have at least one substituent. Examples of substituents include a straight or branched lower alkyl, lower alkoxy, or lower alkyl-carbonyl group that may be substituted with one or more halogen atoms; amino; hydroxyl; carbamoyl; an unsaturated heterocyclic ring; an aromatic ring; nitro: amido; an ester group; carboxyl; hydroxyl; cyano; a halogen atom; a group represented by formula (a):-Si(R$^{1'}$)$_m$(OR$^{2'}$)$_{3-m}$ (in formula (a), m and R$^a$ are the same as in the above formula); and the like. Specific examples thereof include those exemplified in the above-mentioned explanation of R$^1$. The number of substituents is, for example, 1 to 3, and preferably 1 to 2.

Ring A is bonded to each other via or not via one or more heteroatoms to form an optionally substituted unsaturated hydrocarbon ring, an optionally substituted unsaturated heterocyclic ring, or an optionally substituted aromatic ring. Ring A may be monocyclic or polycyclic.

The unsaturated heterocyclic ring or the aromatic ring may be monocyclic or polycyclic, and each ring is preferably a 5- to 10-membered ring, and more preferably a 5- to 6-membered ring. Examples of the unsaturated hydrocarbon ring, the unsaturated heterocyclic ring, and the aromatic ring that may have one or more heteroatoms include pyridine ring, pyrrole ring, oxazole ring, isoxazole ring, thiazole ring, isothiazole ring, furazan ring, imidazole ring, pyrazole ring, pyrazine ring, pyrimidine ring, pyridazine ring, dihydrooxazole ring, thiophene ring, furan ring, pyrazole ring, benzene ring, naphthalene ring, phenanthrene ring, and the like. Two or more of these rings may be fused to form a polycyclic ring.

The unsaturated hydrocarbon ring, the unsaturated heterocyclic ring, or the aromatic ring may have at least one substituent. Examples of substituents include a straight or branched lower alkyl, lower alkoxy, or lower alkyl-carbonyl group that may be substituted with one or more halogen atoms; amino; hydroxyl; carbamoyl; an unsaturated heterocyclic ring; an aromatic ring; nitro; amido; an ester group; carboxyl; hydroxyl; cyano; a halogen atom; a group represented by formula (a):-Si($R^{1'}$)$_m$(O$R^{2'}$)$_{3-m}$ (in formula (a), m, $R^{1'}$, and $R^{2'}$ are the same as in the above formula); and the like. Specific examples thereof include those exemplified in the above-mentioned explanation of $R^1$. The number of substituents is, for example, 1 to 3, and preferably 1 to 2.

$Z^1$ is a carbon atom or a heteroatom. Examples of the heteroatom include nitrogen atom, oxygen atom, and sulfur atom. When $Z^1$ is a heteroatom other than a nitrogen atom (for example, oxygen atom or sulfur atom), $R^2$ is absent, and when $Z^1$ is a nitrogen atom, $Z^1$ has $R^2$ ($Z^1$ is —N$R^2$—) or does not have $R^2$ ($Z^1$ is —N=). When $Z^1$ is a carbon atom, $Z^1$ has one $R^2$ ($Z^1$ is —C$R^2$=) or two $R^2$s ($Z^1$ is —C($R^2$)$_2$—).

Specific examples of formula (1a) include the following:

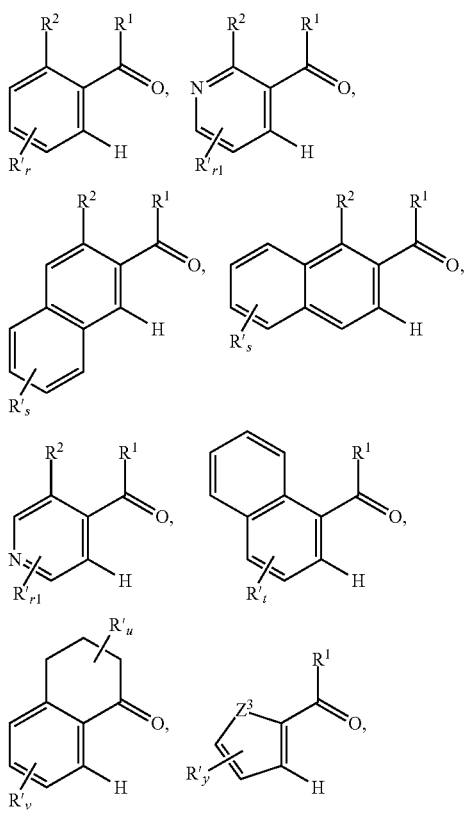

-continued

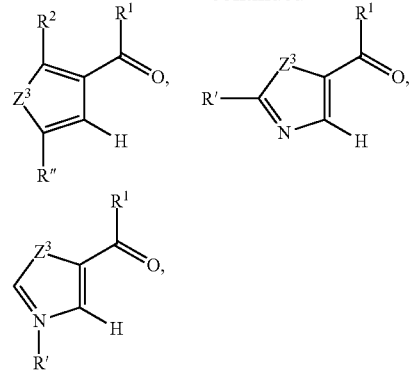

wherein $R^1$ and $R^2$ are the same as in the above formula (1a); $Z^3$ is a heteroatom; r is an integer of 1 to 3; r1 is an integer of 1 to 2; s is an integer of 1 to 5; t is an integer of 1 to 6; u is an integer of 1 to 6; v is an integer of 1 to 3; y is 1 or 2; R' and R" are each the same as the substituents exemplified in $R^1$ of the aforementioned formula (1a); and when r, r1, s, t, u, v, or y is two or more, R's may be the same or different.

In formula (1b), E and $R^1$ are, for example, the same as those mentioned above in formula (1a).

$R^3$ is, for example, a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-Si($R^{1'}$)$_m$(O$R^{2'}$)$_{3-m}$ (in formula (a), m, $R^{1'}$, and $R^{2'}$ are the same as in the above formula). Specific examples thereof include those exemplified in the above-mentioned explanation of $R^1$.

$R^1$ and $R^3$ may be bonded to each other via or not via one or more heteroatoms to form an optionally substituted saturated hydrocarbon ring, an optionally substituted unsaturated heterocyclic ring, or an optionally substituted aromatic ring. Examples of the saturated hydrocarbon ring include cyclopentane ring and cyclohexane ring.

The saturated hydrocarbon ring, the unsaturated heterocyclic ring, or the aromatic ring is preferably a 5- to 10-membered ring and more preferably a 5- to 6-membered ring.

Specific examples of the saturated hydrocarbon ring, the unsaturated heterocyclic ring, the aromatic ring, and the substituent(s) thereof include those exemplified in the above-mentioned explanation of the optionally substituted unsaturated heterocyclic ring or optionally substituted aromatic ring, and substituent(s) thereof of $R^1$ and $R^2$. In addition, saturated hydrocarbon rings, such as cyclohexane and cyclopentane, can be mentioned.

$R^4$ is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-Si($R^{1'}$)$_m$(O$R^{2'}$)$_{3-m}$ (in formula (a), m, $R^{1'}$, and $R^{2'}$ are the same as in the above formula). Specific examples thereof include those exemplified in the above-mentioned explanation of $R^1$.

$Z^2$ is a carbon atom or a nitrogen atom, and n is 1 or 2. When $Z^2$ is a carbon atom, n is 2 and $R^4$s may be the same or different. When $Z^2$ is a nitrogen atom, n is 1.

In formula (1c), E and $R^1$ are the same as those mentioned in formula (1a). $R^3$ in formula (1c) is the same as that mentioned above in formula (1b).

$R^5$ is, for example, a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-Si$(R^{1'})_m$ $(OR^{2'})_{3-m}$ (in formula (a), m, $R^{1'}$, and $R^{2'}$ are the same as in the above formula). Specific examples thereof include those exemplified in the above-mentioned explanation of $R^1$.

Compound (2) is represented by formula (2):

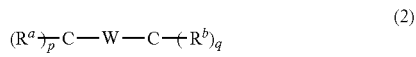

wherein $R^a$, $R^b$, p, q, and W are as defined above.

In formula (2), $R^a$ and $R^b$ may be the same or different and each is, for example, a hydrogen atom, a straight or branched lower alkyl, lower alkoxy, or lower alkyl-carbonyl group that may be substituted with one or more halogen atoms, lower alkenyl, lower alkynyl, carbamoyl, an unsaturated heterocyclic ring, an aromatic ring, nitro, amino, amido, an ester group, carboxyl, hydroxyl, cyano, a halogen atom, or a group represented by formula (a):-Si$(R^{1'})_m(OR^{2'})_{3-m}$ (in formula (a), m, $R^{1'}$, and $R^{2'}$ are the same as in the above formula). Specific examples thereof include those exemplified in the above-mentioned explanation of $R^2$.

Examples of the straight or branched lower alkenyl include straight or branched lower alkenyl having about 2 to about 4 carbon atoms, such as vinyl, allyl, and butenyl.

Examples of the straight or branched lower alkynyl include straight or branched lower alkynyl having about 2 to about 4 carbon atoms, such as ethynyl, propynyl, and butynyl.

p and q are each 1 or 2. When W is a double bond, p and q are each 2. When W is a triple bond, p and q are each 1.

Specific examples of formula (2) include the following:

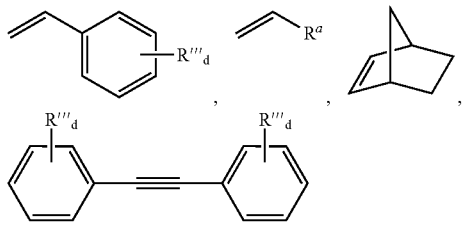

wherein $R^a$ is the same as in the aforementioned formula (2); $R'''$s are each the same as the substituents exemplified in $R^1$ of the aforementioned formula (1a); and d is an integer of 1 to 5.

The amount of compound (2) is not particularly limited. To ensure, from an industrial perspective, that no unreacted raw materials remain, compound (2) may be added in an equimolar amount per mol of compound (1), or compound (1) or compound (2) may be added in a large excess amount. Compound (2) may be added in an amount of 0.1 to 10 mol, preferably 1 to 4 mol, and more preferably 1 to 2 mol per mole of compound (1).

Compound (3) represented by the following formula (3a), (3b), or (3c) is produced by the production method of the present invention.

Formula (3a):

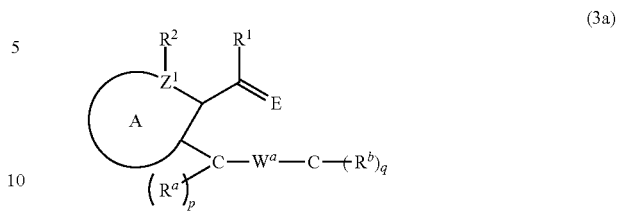

in formula (3a), E, A, $Z^1$, $R^1$, and $R^2$ are the same as defined in formula (1a) above; $R^a$, $R^b$, p, and q are the same as defined in formula (2) above; and $W^a$ is a single bond or a double bond; Formula (3b):

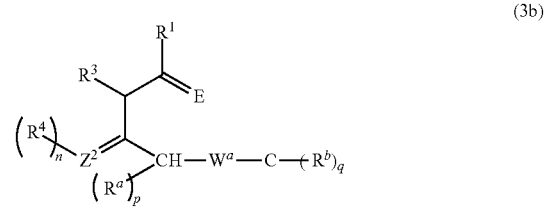

in formula (3b), $Z^2$, $R^1$, $R^3$, $R^4$ and n are the same as defined in formula (1b) above; $R^a$, $R^b$, p, and q are the same as defined in formula (2) above; and $W^a$ is the same as defined in formula (3a) above; or
Formula (3c):

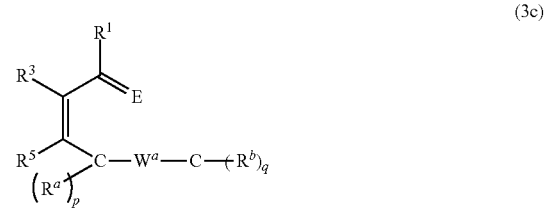

in formula (3c), $R^1$, $R^3$, and $R^5$ are the same as defined in formula (1c) above; $R^a$, $R^b$, p, and q are the same as defined in formula (2) above; $W^a$ is the same as defined in formula (3a) above.

In the production method of the present invention, even if a small amount of water is contained in the reaction system, the reaction proceeds, and compound (3) can be produced. In the reaction system, the reaction is preferably carried out under an inert gas atmosphere. Examples of inert gases include argon, nitrogen, helium, and the like.

Further, in the present invention, compound (3) may be produced in the presence of an organic solvent. Compound (3) may also be produced with no solvent.

When compound (3) is produced in the presence of an organic solvent, examples of the organic solvent include non-polar solvents, such as mesitylene, xylene, toluene, benzene, hexane, n-octane, and n-decane; and polar solvents, such as N-methyl-2-pyrrolidone (hereafter, may be referred to as NMP), dimethylformamide, THF, dioxane, and methylene chloride. Of these, non-polar solvents are preferable from the viewpoint of improving the yield of compound (3). More specifically, toluene, mesitylene, and the like are particularly preferable.

The reaction temperature is preferably about 40 to about 200° C., and more preferably about 80 to about 150° C.

Since the ruthenium catalyst used in the present invention is a metal oxide-supported heterogeneous catalyst, the production method of the present invention is performed in a solid phase-liquid phase process. Thus, for example, the production method of the present invention can be applied to a method in which a reaction is continuously carried out, i.e., a method in which the metal oxide-supported ruthenium catalyst of the present invention is placed into a column, etc., and starting materials, etc., are passed through to obtain compound (3); a method in which the metal oxide-supported ruthenium catalyst of the present invention, starting materials, etc., are dispersed in a solution, and the catalyst and the product are separated by filtration or decantation method after the reaction; and other methods.

Compound (3) produced by the production method of the present invention can be used as raw materials for pharmaceuticals, raw materials for agricultural chemicals, liquid crystal materials, electronic materials, macromolecular monomers, and the like. The production method of the present invention is useful as an efficient and low environmental burden-type method for producing compound (3). A carbon-carbon bond formation reaction accompanied by activation of an aromatic carbon-hydrogen bond is utilized, for example, for synthesis of precursors of antihypertensive agents (angiotensin II receptor antagonists). However, current processes, which use a homogeneous catalyst, impose a heavy burden on the environment and energy at the stage of removing the catalyst component from the product. On the other hand, the production method of the present invention, which uses a heterogeneous catalyst, makes it possible to reduce the cost of removing the catalyst component, and thus can be expected to be usefully used.

EXAMPLES

Examples and Comparative Examples are given below to illustrate the present invention in more detail; however, the present invention is not limited to the following examples.

Synthesis Example 1

Preparation of $Ru/CeO_2$

Ruthenium supported on cerium oxide ($Ru/CeO_2$) was obtained by dissolving tris(acetylacetonate)ruthenium (produced by Aldrich) in about 10 mL of tetrahydrofuran (THF) in such an amount as to obtain a ruthenium loading of 2% by mass, adding 1.0 g of cerium oxide prepared by the methods disclosed in H. Miura, K. Wada, S. Hosokawa, M. Inoue, ChemCatChem 2010, 2, 1223-1225 (Non-patent Literature 1) and JP2010-018488A thereto to be impregnated at room temperature, and evaporating the resulting product to dryness, followed by calcination in air at 400° C. for 30 minutes.

Synthesis Example 2

Preparation of $(HCHO+4PPh_3)$-$Ru/CeO_2$

A 20 mL Pyrex® reaction vessel was charged with 125 mg of $Ru/CeO_2$ prepared in Synthesis Example 1 (containing 0.025 mmol as Ru), 26.3 mg (0.10 mmol) of triphenylphosphine, 0.25 mL of 36% by mass formalin solution, and 2 mL of 2-methoxyethanol. The mixture was stirred with heating at 130° C. on a hot plate under an argon gas atmosphere for 30 minutes, and the volatile components were evaporated under reduced pressure at room temperature. The thus-obtained solid was designated as $(HCHO+4PPh_3)$-$Ru/CeO_2$.

Synthesis Example 3

Preparation of $(HCHO+4PPh_3)$-$Ru/ZrO_2$ $(HCHO+4PPh_3)$-$Ru/ZrO_2$ was prepared in the same manner as in Synthesis Example 2 except that $Ru/ZrO_2$ was used instead of $Ru/CeO_2$.

Synthesis Example 4

Preparation of $4PPh_3$-$Ru/CeO_2$ $4PPh_3$-$Ru/CeO_2$ was prepared by the method disclosed in Non-patent Literature 1. More specifically, a 20 mL Pyrex® reaction vessel was charged with 125 mg of $Ru/CeO_2$ prepared in Synthesis Example 1 (containing 0.025 mmol as Ru) and 26.3 mg (0.10 mmol) of triphenylphosphine, and the mixture was kept at 100° C. for 20 minutes under a hydrogen atmosphere (1 atm) to give $4PPh_3$-$Ru/CeO_2$.

Synthesis Example 5

Preparation of $(4PPh_3)$-$Ru/CeO_2$

A 20 mL Pyrex® reaction vessel containing a magnetic stirrer was charged with 125 mg of $Ru/CeO_2$ prepared in Synthesis Example 1 (containing 0.025 mmol as Ru), 26.3 mg (0.10 mmol) of triphenylphosphine, and 2 mL of 2-methoxyethanol. The mixture was stirred with heating at 130° C. on a hot plate under an argon gas atmosphere for 30 minutes, and the volatile components were evaporated under reduced pressure at room temperature. The thus-obtained solid was designated as $(4PPh_3)$-$Ru/CeO_2$.

Synthesis Examples 6 to 9

Preparation of Ru Catalysts

Ru catalysts were prepared in the same manner as in Synthesis Example 1, except that $SiO_2$ (CAB-O-SIL® (produced by Cabot Japan)) (Synthesis Example 6), $Al_2O_3$ (JRC-ALO-8 (Catalysis Society of Japan reference catalyst) (Synthesis Example 7), $TiO_2$ (JRC-TIO-4 (Catalysis Society of Japan reference catalyst)) (Synthesis Example 8), and MgO (Synthesis Example 9) were respectively used instead of $CeO_2$.

Synthesis Examples 10 to 13

Preparation of $(HCHO+4PPh_3)$-Ru Catalysts $(HCHO+4PPh_3)$-Ru catalysts were prepared by the method of Synthesis Example 2 except that $Ru/SiO_2$, $Ru/Al_2O_3$, $Ru/TiO_2$, and $Ru/MgO$ prepared in Synthesis Examples 6 to 9, respectively, were respectively used instead of $Ru/CeO_2$.

Example 1

A 20 mL Pyrex® reaction vessel containing a magnetic stirrer was charged with $(HCHO+4PPh_3)$-$Ru/CeO_2$ (0.050 mmol as Ru) prepared in Synthesis Example 2. After the atmosphere in the vessel was replaced with argon, 1.0 mmol of α-tetralone (1a), 3.0 mmol of styrene (2a), and 2.0 mL of toluene as a solvent were added thereto, and a reaction was carried out for 3 hours under an argon atmosphere on a hot plate equipped with a reflux condenser and maintained at 140° C. to synthesize compounds (3aa and 4aa) shown in Reaction Scheme (A), in which the aromatic C—H bond was inserted regioselectively to the vinyl group, as a mixture of two regioisomers. The reaction vessel was equipped with a rubber balloon filled with argon. The obtained compounds (3aa and 4aa) were measured qualitatively and quantitatively by means of NMR (EX-400 produced by JEOL Ltd.), GC-MS (Parvum 2 produced by Shimazu Corporation), and GC (GC353 produced by GL Sciences Inc.).

Reaction Scheme (A) shows the reaction of Example 1, and Table 1 shows the yield of compounds (3aa and 4aa) obtained in Example 1, and the isomer ratio thereof.

Example 2

The synthesis of compounds (3aa and 4aa) was carried out under the same conditions as in Example 1, except that the Ru catalyst ((HCHO+4PPh$_3$)-Ru/ZrO$_2$) prepared in Synthesis Example 3 was used as a catalyst.

Comparative Example 1

The synthesis of compounds (3aa and 4aa) was carried out under the same conditions as in Example 1, except that the Ru catalyst prepared in Synthesis Example 1 was used as a catalyst and 0.20 mmol of PPh$_3$ was added as an additive.

Comparative Examples 2 and 3

The synthesis of compounds (3aa and 4aa) was carried out under the same conditions as in Example 1 except that the Ru catalyst individually prepared in each of Synthesis Examples 10 to 13 was used as a catalyst.

Table 1 shows the results of the effects of various catalysts on the reaction between α-tetralone (1a) and styrene (2a) in Examples 1 and 2 and Comparative Examples 1 to 8.

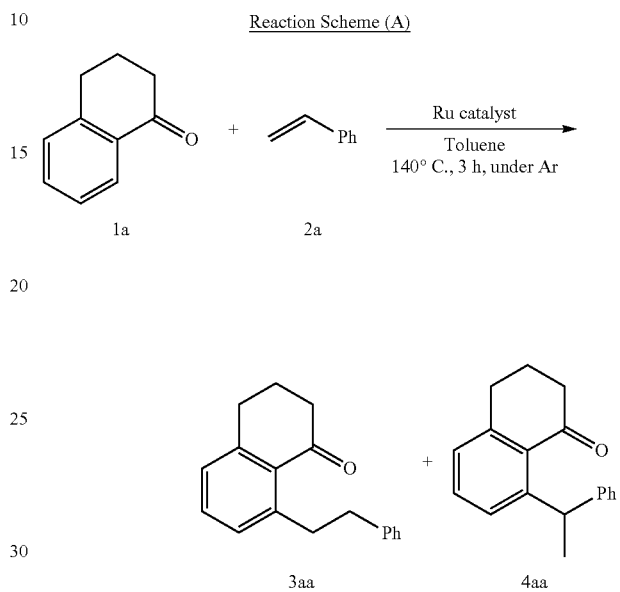

TABLE 1

| Example No. | Ru Catalyst | Lower Alcohol Compound | Additive | Yield 3aa + 4aa (%) | Isomer Ratio 3aa : 4aa |
|---|---|---|---|---|---|
| Ex. 1 | (HCHO + 4PPh$_3$)-Ru/CeO$_2$ (Synthesis Ex. 2) | HO-CH$_2$CH2-OMe | — | 85 | 75 : 25 |
| Ex. 2 | (HCHO + 4PPh$_3$)-Ru/ZrO$_2$ (Synthesis Ex. 3) | HO-CH$_2$CH2-OMe | — | 98 | 76 : 24 |
| Comp. Ex. 1 | Ru/CeO$_2$ (Synthesis Ex. 1) | — | PPh$_3$ (0.20 mmol) | 0 | — |
| Comp. Ex. 2 | 4PPh$_3$-Ru/CeO$_2$ (Synthesis Ex. 4) | — | — | 0 | — |
| Comp. Ex. 3 | 4PPh$_3$-Ru/CeO$_2$ (Synthesis Ex. 5) | HO-CH2CH2-OMe | — | 0 | — |
| Comp. Ex. 4 | Ru/CeO$_2$ (Synthesis Ex. 1) | — | PPh$_3$ (0.20 in mol) + 36% Formalin Solution (0.50 mL) | 0 | — |
| Comp. Ex. 5 | (HCHO + 4PPh$_3$)-Ru/SiO$_2$ (Synthesis Ex. 10) | HO-CH$_2$CH2-OMe | — | 0 | — |
| Comp. Ex. 6 | (HCHO + 4PPh$_3$)-Ru/Al$_2$O$_3$ (Synthesis Ex. 11) | HO-CH$_2$CH2-OMe | — | 0 | — |
| Comp. Ex. 7 | (HCHO + 4PPh$_3$)-Ru/TiO$_2$ (Synthesis Ex. 12) | HO-CH$_2$CH2-OMe | — | 0 | — |
| Comp. Ex. 8 | (HCHO + 4PPh$_3$)-Ru/MgO (Synthesis Ex. 13) | HO-CH$_2$CH2-OMe | — | 0 | — |

Reaction Conditions: 1 a (1.0 mmol), 2 a (3.0 mmol), Toluene (2.0 mL), Ru Catalyst (0.050 mmol as Ru Metal), Reaction Temperature (140° C.), Reaction Time (3 hours), Under Argon Atmosphere catalyst individually prepared in each of Synthesis Example 4 and Synthesis Example 5 was used as a catalyst.

Comparative Example 4

The synthesis of compounds (3aa and 4aa) was carried out under the same conditions as in Example 1 except that the Ru catalyst prepared in Synthesis Example 1 was used as a catalyst and 0.20 mmol of PPh$_3$ as an additive and 0.5 mL of a formalin solution (concentration: 36%) were added.

Comparative Examples 5 to 8

The synthesis of compounds (3aa and 4aa) was carried out under the same conditions as in Example 1 except that the Ru <Results and Discussion>

Only the (HCHO+4PPh$_3$)-Ru/CeO$_2$ catalyst and the (HCHO+4PPh$_3$)-Ru/ZrO$_2$ catalyst, each of which was pretreated by the method in which triphenylphosphine and the formalin solution were used, exhibited activity in the reaction shown in Reaction Scheme (A), resulting in a good yield of the desired alkyl-substituted aromatic compounds. The (4PPh$_3$)-Ru/CeO$_2$ catalyst (Comparative Example 1), which was prepared in the same manner but to which the formalin solution was not added, exhibited no activity in the reaction shown in Reaction Scheme (A). The above results indicate that pretreatment in the presence of a formalin solution is essential for exhibiting activity. As shown in Comparative Examples 2 and 3, when the Ru/CeO$_2$ catalysts (Synthesis Examples 4 and 5) used in Non-patent Literature 1 and JP2010-018488A were used, the reaction shown in Reaction Scheme (A) did not proceed at all. Further, each catalyst in which ruthenium was supported on a support other than CeO$_2$ and ZrO$_2$, and that was pretreated by the method in which triphenylphosphine and the formalin solution were used, also exhibited no activity.

Examples 3 to 10

A 20 mL Pyrex® reaction vessel containing a magnetic stirrer was charged with (HCHO+4PPh$_3$)-Ru/CeO$_2$ (0.025 mmol as Ru) prepared in Synthesis Example 2. After the atmosphere in the vessel was replaced with argon, 0.5 mmol of α-tetralone (1a), 3.0 mmol of alkene (2b) to (2k) shown in Table 2 (1.0 mmol for 2e), and 1.0 mL of toluene as a solvent were added thereto, and a reaction was carried out under an argon atmosphere for the reaction time shown in Table 2 on a hot plate equipped with a reflux condenser while maintaining the temperature shown in Table 2 to synthesize compounds (3 and 4) shown in Reaction Scheme (B), in which the aromatic C—H bond was inserted regioselectively to the vinyl group, as a mixture of two regioisomers. The reaction vessel was equipped with a rubber balloon filled with argon. The obtained compounds (3 and 4) were measured qualitatively and quantitatively in the same manner as in Example 1.

Reaction Scheme (B) shows the reaction of Examples 3 to 10, and Table 2 shows the yields of compounds (3 and 4) individually obtained in Examples 3 to 10 and the individual isomer ratio thereof.

Reaction Scheme (B)

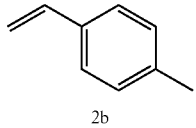

TABLE 2

| Example No. | Compound 2 | Temperature (°C.) | Reaction Time (h) | Yield 3 + 4 (%) | Isomer Ratio 3:4 |
|---|---|---|---|---|---|
| 3 | 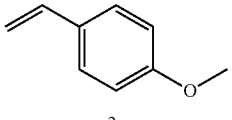 2b | 140 | 3 | 90 | 75:25 |
| 4 | 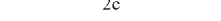 2c | 140 | 4 | 99 | 74:26 |
| 5 | 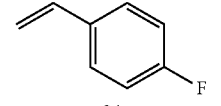 2d | 140 | 4 | 94 | 70:30 |
| 6 | 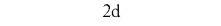 2e | 140 | 0.5 | 99 | 100:0 |
| 7 | 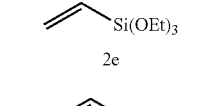 2f | 120 | 24 | 74 | 100:0 |
| 8 |  2g | 140 | 6 | 84 | 100:0 |
| 9 | 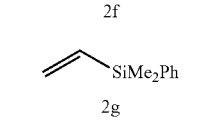 2j | 140 | 6 | 78 | — |
| 10 |  2k | 140 | 24 | trace | — |

Reaction Conditions: 1a (0.50 mmol), 2 (1.5 mmol) (but 1.0 mmol for 2e), Toluene (1.0 mL), Ru Catalyst (0.025 mmol as Ru Metal), Under Argon Atmosphere <Results and Discussion>

It was confirmed that (HCHO+4PPh$_3$)-Ru/CeO$_2$ synthesized in Synthesis Example 2 was also effective in the reactions with alkenes (2b) to (2k) shown in Table 2. In particular, when alkenes 2b to 2j were used, the desired products were obtained in a high yield in a very short period of time.

The hitherto known solid catalysts (such as 4PPh$_3$-Ru/CeO$_2$) obtained in Non-patent Literature 1 were only applicable to triethoxyvinylsilane and dimethylethoxyvinylsilane. In reactions in which other alkenes were used as a raw material, the hitherto known solid catalysts exhibited no activity, yielding no desired products. Further, the shortest time required to complete the reactions between α-tetralone and triethoxysilane that use the solid catalysts obtained by the hitherto known method was 90 minutes. On the other hand, when (HCHO+4PPh$_3$)-Ru/CeO$_2$ was used, the reaction was completed within 30 minutes, which indicates that the desired product can be obtained efficiently.

Examples 11 to 14

A 20 mL Pyrex® reaction vessel containing a magnetic stirrer was charged with (HCHO+4PPh$_3$)-Ru/CeO$_2$ (0.025 mmol as Ru) prepared in Synthesis Example 2. After the atmosphere in the vessel was replaced with argon, 0.5 mmol of aromatic compound (1) shown in Table 3, 1.5 mmol of styrene, and 1.0 mL of toluene as a solvent were added thereto. A reaction was carried out for 3 hours under an argon atmosphere on a hot plate equipped with a reflux condenser and maintained at 140° C., and a reaction was carried out for the reaction time shown in Table 3 to synthesize compounds (3 and 4) shown in Reaction Scheme (C), in which the aromatic C—H bond was inserted regioselectively to the vinyl group, as a mixture of two regioisomers. The reaction vessel was equipped with a rubber balloon filled with argon. The obtained compounds (3 and 4) were measured qualitatively and quantitatively in the same manner as in Example 1.

Reaction Scheme (C) shows the reaction of Examples 11 to 14, and Table 3 shows the yields of compounds (3 and 4) individually obtained in Examples 11 to 14, and the individual isomer ratio thereof.

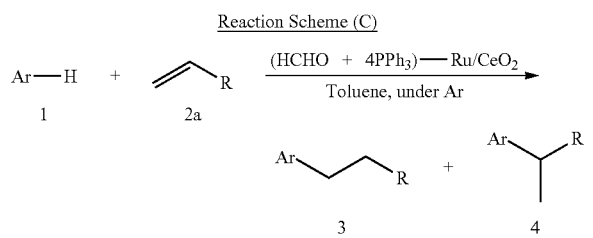

TABLE 3

| Example No. | Compound 1 | Reaction Time (h) | Yield 3 + 4 (%) | Sel. (3:4) |
|---|---|---|---|---|
| 11 | 1c | 3 | 99 | 25:75 |
| 12 | 1e | 24 | 67 | 77:23 |
| 13 | 1f | 3 | 98 | 75:25 |
| 14 | 1g | 6 | 75 | 75:25 |

Reaction Conditions: 1 (0.50 mmol), 2a (1.5 mmol), Toluene (1.0 mL), Ru Catalyst (0.025 mmol as Ru Metal), Reaction Temperature 140° C., Under Argon Atmosphere <Results and Discussion>

(HCHO+4PPh$_3$)-Ru/CeO$_2$ obtained in Synthesis Example 2 was effective in the reactions with the various aromatic compounds as shown in Table 3, and the desired products were obtained in high yields in a very short period of time. On the other hand, the hitherto known solid catalysts (such as 4PPh$_3$-Ru/CeO$_2$) disclosed in Non-patent Literature 1 and JP2010-018488A exhibited no activity on any of the reactions like the reactions of Examples 11 to 14.

Example 15

A 20 mL Pyrex® reaction vessel containing a magnetic stirrer was charged with (HCHO+4PPh$_3$)-Ru/CeO$_2$ (0.025 mmol as Ru) prepared in Synthesis Example 2. After the atmosphere in the vessel was replaced with argon, 1.2 mmol of α-tetralone (1a), 1.0 mmol of diphenylacetylene (5), and 1.0 mL of toluene as a solvent were added thereto, and a reaction was carried out for 6 hours under an argon atmosphere on a hot plate equipped with a reflux condenser and maintained at 140° C. to synthesize compound (6a) shown in Reaction Scheme (D). The yield of compound (6a) was 88%. The reaction vessel was equipped with a rubber balloon filled with argon. The obtained compound (6a) was measured qualitatively and quantitatively in the same manner as in Example 1.

Reaction Scheme (D) shows the reaction of Example 15.

Example 16

The Ru catalyst used in Example 15 was separated from the reaction system, washed with diethyl ether, dried at 80° C. overnight, and calcined at 400° C. in air for 30 minutes. A 20 mL Pyrex® reaction vessel was charged with 125 mg of Ru/CeO$_2$ (containing 0.025 mmol as Ru) obtained by the calcination, 26.3 mg (0.10 mmol) of triphenylphosphine, 0.25 mL of 36% by mass formalin solution, and 2 mL of 2-methoxyethanol. The mixture was stirred with heating at 140° C. under an argon gas atmosphere on a hot plate for 30 minutes, and the volatile components were evaporated under reduced pressure at room temperature to give solid (HCHO+4PPh$_3$)-Ru/CeO$_2$.

α-tetralone (1a) was reacted with diphenylacetylene (5) in the same manner as in Example 15 by using the catalyst (HCHO+4PPh$_3$)-Ru/CeO$_2$ obtained by the above method to synthesize compound (6a) shown in Reaction Scheme (D). The obtained compound (6a) was measured qualitatively and quantitatively in the same manner as in Example 1. The yield of the compound (6a) was 88%.

Reaction Scheme (D) shows the reaction of Example 16.

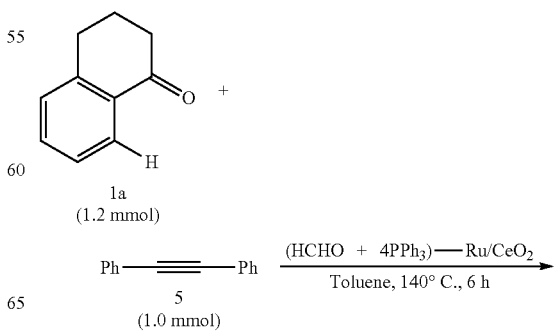

-continued

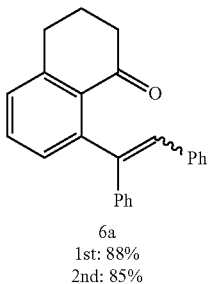

6a
1st: 88%
2nd: 85%

<Results and Discussion>

Example 15 shows that the catalyst ((HCHO+4PPh$_3$)-Ru/CeO$_2$) synthesized in Synthesis Example 2 is effective in a reaction with diphenylacetylene, and the desired alkenyl-substituted aromatic compound was obtained in a high yield in a very short period of time.

Also in Example 16, in which the catalyst used in Example 15 was separated and recovered, and the synthesis of the compound was carried out in the same manner as in Example 15, the desired alkenyl-substituted aromatic compound was obtained in a high yield in a very short period of time as in Example 15, with little decrease in catalytic activity. Thus, it was found that the Ru catalyst synthesized in Synthesis Example 2 can be recycled.

The hitherto known solid catalysts (such as 4PPh$_3$-Ru/CeO$_2$) disclosed in Non-patent Literature 1 and JP2010-018488A exhibited no activity on the reaction like the reactions of Examples 15 and 16.

Example 17

A 20 mL Pyrex® reaction vessel containing a magnetic stirrer was charged with (HCHO+4PPh$_3$)-Ru/CeO$_2$ (0.050 mmol as Ru) prepared in Synthesis Example 2. After the atmosphere in the vessel was replaced with argon, 1.0 mmol of 2-acetylthiophene (1f), 3.0 mmol of styrene (2a), and 2.0 mL of toluene as a solvent were added thereto, and a reaction was carried out for 6 hours under an argon atmosphere on a hot plate equipped with a reflux condenser and maintained at 140° C. to synthesize compounds (3fa and 4fa) shown in Reaction Scheme (E), in which the aromatic C—H bond was inserted regioselectively to the vinyl group, as a mixture of two regioisomers. The reaction vessel was equipped with a rubber balloon filled with argon. The obtained compounds (3fa and 4fa) were measured qualitatively and quantitatively in the same manner as in Example 1. The yield of the compounds (3fa and 4fa) was 99%.

Reaction Scheme (E) shows the reaction of Example 17.

Example 18

The Ru catalyst used in Example 17 was separated from the reaction system, washed with diethyl ether, dried at 80° C. overnight, and calcined at 400° C. in air for 30 minutes. A 20 mL Pyrex® reaction vessel was charged with 125 mg of Ru/CeO$_2$ (containing 0.025 mmol as Ru) obtained by the calcination, 26.3 mg (0.10 mmol) of triphenylphosphine, 0.25 mL of 36% by mass formalin solution, and 2 mL of 2-methoxyethanol. The mixture was stirred with heating at 140° C. under an argon gas atmosphere on a hot plate for 30 minutes, and the volatile components were evaporated under reduced pressure at room temperature to give solid (HCHO+4PPh$_3$)-Ru/CeO$_2$.

2-acetylthiophene (1f) was reacted with styrene (2a) in the same manner as in Example 17 by using the catalyst (HCHO+4PPh$_3$)-Ru/CeO$_2$ obtained by the above method to synthesize compounds (3fa and 4fa) shown in Reaction Scheme (E). The yield of compounds (3fa and 4fa) was 99%. The obtained compounds (3fa and 4fa) were measured qualitatively and quantitatively in the same manner as in Example 1.

Reaction Scheme (E) shows the reaction of Example 18.

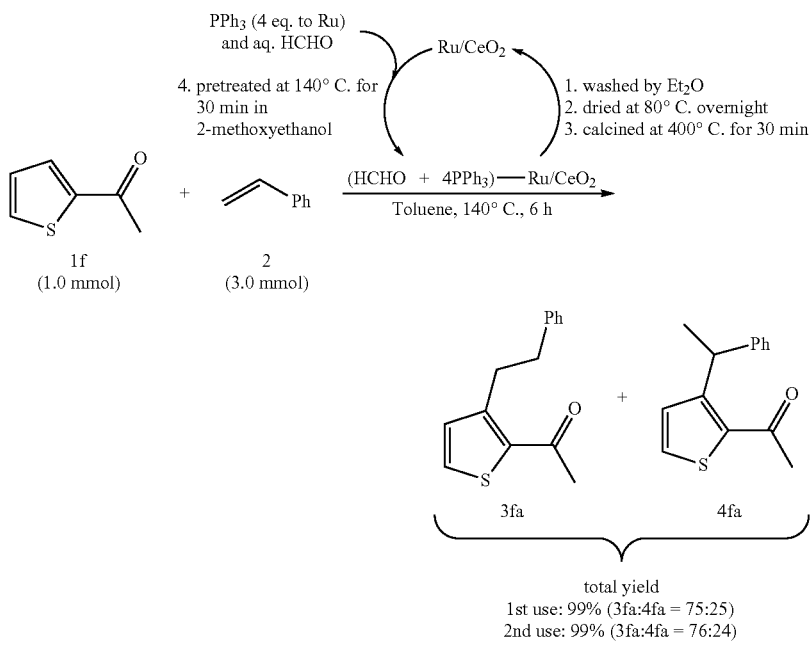

Reaction Scheme (E)

total yield
1st use: 99% (3fa:4fa = 75:25)
2nd use: 99% (3fa:4fa = 76:24)

<Results and Discussion>

Examples 17 and 18 show the following. As in Example 17, the desired alkenyl-substituted aromatic compounds were also obtained in a high yield in a very short period of time with little decrease in catalytic activity in Example 18, in which the catalyst used in Example 17 was separated and recovered, and the synthesis of the compounds was carried out in the same manner as in Example 17. Thus, it was found that the Ru catalyst synthesized in Synthesis Example 2 can also be recycled in the system shown in Reaction Scheme (E).

The hitherto known solid catalysts (such as 4PPh$_3$-Ru/CeO$_2$) disclosed in Non-patent Literature 1 and JP2010-018488A exhibited no activity on the reaction like the reactions of Examples 17 and 18.

Synthesis Example 14

Preparation of (HCHO+4PPh$_3$)-Ru/ZrO$_2$ (HCHO+4PPh$_3$)-Ru/ZrO$_2$ was prepared in the same manner as in Synthesis Example 3 except that the amount of triphenylphosphine was 13.2 mg.

Synthesis Example 15

Preparation of (HCHO+4PPh$_3$)-Ru/ZrO$_2$ (HCHO+4PPh$_3$)-Ru/ZrO$_2$ was prepared in the same manner as in Synthesis Example 3 except that tris(acetylacetonate)ruthenium (produced by Aldrich) was used in such an amount as to obtain a ruthenium loading of 1% by mass.

Synthesis Example 16

Preparation of (HCHO+4PPh$_3$)-Ru/ZrO$_2$ (HCHO+4PPh$_3$)-Ru/ZrO$_2$ was prepared in the same manner as in Synthesis Example 15 except that the amount of triphenylphosphine was 13.2 mg.

Synthesis Example 17

Preparation of (HCHO+4PPh$_3$)-Ru/ZrO$_2$ (HCHO+4PPh$_3$)-Ru/ZrO$_2$ was prepared in the same manner as in Synthesis Example 16 except that tris(acetylacetonate)ruthenium (produced by Aldrich) was used in such an amount as to obtain a ruthenium loading of 0.5% by mass.

Example 19

A 20 mL Pyrex® reaction vessel containing a magnetic stirrer was charged with (HCHO+4PPh$_3$)-Ru/ZrO$_2$ (0.025 mmol as Ru) prepared in Synthesis Example 3. After the atmosphere in the vessel was replaced with argon, 0.5 mmol of α-tetralone (1a), 1.5 mmol of alkene (2g), and 1.0 mL of toluene as a solvent were added thereto, and a reaction was carried out under an argon atmosphere for 3 hours while maintaining the temperature at 140° C. on a hot plate equipped with a reflux condenser to synthesize compound (3g), in which the aromatic C—H bond was inserted regioselectively to the vinyl group. The reaction vessel was equipped with a rubber balloon filled with argon. The obtained compound (3g) was measured qualitatively and quantitatively in the same manner as in Example 1.

Examples 20 to 26

The synthesis of compound (3g) was carried out under the same conditions as in Example 19 except that the Ru catalyst ((HCHO+4PPh$_3$)-Ru/ZrO$_2$) individually prepared in each of Synthesis Examples 14 to 17 (0.0125 mmol to 0.0063 mmol as Ru) was used as a catalyst (note that the reaction time was 6 hours for only Example 24)

Table 4 shows the yields of the compounds obtained in Examples 19 to 26.

TABLE 4

| Example No. | Ru Catalyst | Ru Catalyst Amount (mmol) | Yield 3 g (%) |
|---|---|---|---|
| Example 19 | (HCHO + 4PPh$_3$)-Ru/ZrO$_2$ (Synthesis Ex. 3) | 0.025 | 77 |
| Example 20 | (HCHO + 4PPh$_3$)-Ru/ZrO$_2$ (Synthesis Ex. 14) | 0.010 | 33 |
| Example 21 | (HCHO + 4PPh$_3$)-Ru/ZrO$_2$ (Synthesis Ex. 14) | 0.0063 | 17 |
| Example 22 | (HCHO + 4PPh$_3$)-Ru/ZrO$_2$ (Synthesis Ex. 15) | 0.0125 | >99 |
| Example 23 | (HCHO + 4PPh$_3$)-Ru/ZrO$_2$ (Synthesis Ex. 16) | 0.0125 | 63 |
| Example 24 | (HCHO + 4PPh$_3$)-Ru/ZrO$_2$ (Synthesis Ex. 16) | 0.0125 | >99 |
| Example 25 | (HCHO + 4PPh$_3$)-Ru/ZrO$_2$ (Synthesis Ex. 16) | 0.0063 | 53 |
| Example 26 | (HCHO + 4PPh$_3$)-Ru/ZrO$_2$ (Synthesis Ex. 17) | 0.0063 | 61 |

Reaction Conditions: 1 a (1.0 mmol), 2 g (3.0 mmol), Toluene (1.0 mL), Reaction Temperature (140° C.), Reaction Time (3 hours; 6 hours for only Example 24), Under Argon Atmosphere <Results and Discussion>

It was confirmed that (HCHO+4PPh$_3$)-Ru/ZrO$_2$ synthesized in Synthesis Example 3 is also effective in a reaction with alkene (2g). Further, when the catalysts shown in Synthesis Examples 15 and 16, which have a ruthenium loading of 1% by mass, were used, the desired compounds were obtained at yields of 99% or more with a smaller amount of ruthenium (Examples 22 and 26). Furthermore, the catalyst (Synthesis Example 17) that has a decreased ruthenium amount of 0.5% by mass exhibited higher catalytic activity per unit amount of ruthenium than the catalyst shown in Synthesis Example 16 (Example 26). These results show that by adjusting the ruthenium loading, a catalyst with higher activity can be prepared, and the amount of ruthenium catalyst required for the reaction can be reduced.

The invention claimed is:

1. A method for producing a ruthenium catalyst, the method comprising mixing
ruthenium supported on at least one metal oxide selected from the group consisting of rare-earth metal oxides, zirconium oxide, and composite oxides containing one or more rare-earth metal oxides and/or zirconium oxide, an aldehyde compound, a phosphorus compound, and
a lower alcohol compound,
and heating the mixture.

2. The method for producing a ruthenium catalyst according to claim 1, wherein the aldehyde compound is at least one member selected from the group consisting of formaldehyde, 1,3,5-trioxane, paraformaldehyde, glyoxal, methylglyoxal, malonaldehyde, acetaldehyde, and propionaldehyde.

3. The method for producing a ruthenium catalyst according to claim 1, wherein the aldehyde compound is formaldehyde.

4. The method for producing a ruthenium catalyst according to claim 1, wherein the phosphorus compound is at least one member selected from the group consisting of phosphines, phosphites, and phosphine oxides.

5. The method for producing a ruthenium catalyst according to claim 1, wherein the phosphorus compound is triphenylphosphine.

6. The method for producing a ruthenium catalyst according to claim 1, wherein the lower alcohol compound is at least one member selected from the group consisting of lower alcohols, lower alkylene glycols, and lower alkoxy-lower alcohols.

7. The method for producing a ruthenium catalyst according to claim 1, wherein the lower alcohol compound is 2-methoxyethanol.

8. The method for producing a ruthenium catalyst according to claim 1, wherein the heating temperature is 40 to 200° C.

9. A method for producing compound (3), comprising:
producing a metal oxide-supported ruthenium catalyst in accordance with the method of claim 1, and
reacting compound (1) having a partial structure of formula (1-1) with a compound represented by formula (2) in the presence of the metal oxide-supported ruthenium catalyst to obtain compound (3) having a partial structure of formula (3-1),

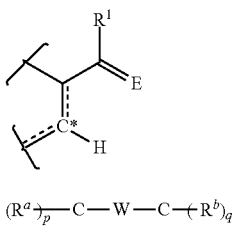

(1-1)

$(R^a)_p$—C—W—C—$(R^b)_q$ (2)

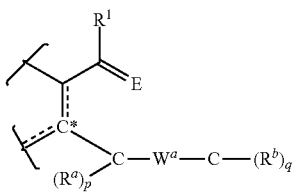

(3-1)

wherein
R$^1$ is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-Si(R$^{1'}$)$_m$(OR$^{2'}$)$_{3-m}$ (in formula (a), m is an integer of 0 to 3, and R$^{1'}$ and R$^{2'}$ may be the same or different and each is lower alkyl or an aromatic ring);

E is an oxygen atom;
R$^a$ and R$^b$ may be the same or different and each is a hydrogen atom, a straight or branched lower alkyl, lower alkoxy, or lower alkyl-carbonyl group that may be substituted with one or more halogen atoms, lower alkenyl, lower alkynyl, carbamoyl, an unsaturated heterocyclic ring, an aromatic ring, nitro, amino, amido, an ester group, carboxyl, hydroxyl, cyano, a halogen atom, or a group represented by formula (a):-Si(R$^{1'}$)$_m$(OR$^{2'}$)$_{3-m}$ (in formula (a), m, R$^{1'}$, and R$^{2'}$ are the same as in the above formula);

R$^a$ and R$^b$ may be combined to form a bicyclo ring;
p and q are each 1 or 2, p and q are each 2 when W is a double bond, and p and q are each 1 when W is a triple bond;
C* is sp$^2$ carbon;
one of two bonds of C* represented by a solid line and a dotted line is a double bond, and the other is a single bond;
W is a double bond or a triple bond; and
W$^a$ is a single bond or a double bond.

10. The method according to claim 9, comprising:
reacting a compound represented by formula (1a) with a compound represented by formula (2) in the presence of the ruthenium catalyst to obtain a compound represented by formula (3a),

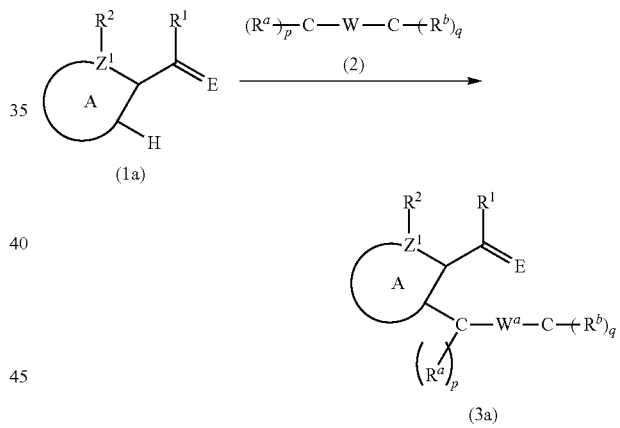

wherein
E is an oxygen atom;
R$^1$ and R$^2$ may be the same or different and each is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-Si(R$^{1'}$)$_m$(OR$^{2'}$)$_{3-m}$ (in formula (a), m is an integer of 0 to 3, and R$^{1'}$ and R$^{2'}$ may be the same or different and each is lower alkyl or an aromatic ring), or
R$^1$ and R$^2$ are bonded to each other via or not via one or more heteroatoms to form a 5- to 10-membered unsaturated hydrocarbon ring, a 5- to 10-membered unsaturated heterocyclic ring, or a 5- to 10-membered aromatic ring, wherein the formed ring may have at least one substituent selected from the group consisting of a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, and a halogen atom;

Ring A is bonded to each other via or not via one or more heteroatoms to form a 5- to 10-membered unsaturated hydrocarbon ring, a 5- to 10-membered unsaturated heterocyclic ring, or a 5- to 10-membered aromatic ring that may have one or more heteroatoms, wherein the formed ring may have at least one substituent selected from the group consisting of a straight or branched lower alkyl, lower alkoxy, or lower alkyl-carbonyl group that may be substituted with one or more halogen atoms, carbamoyl, an unsaturated heterocyclic ring, an aromatic ring, nitro, amino, amido, an ester group, carboxyl, hydroxyl, cyano, a halogen atom, and a group represented by formula (a):-Si$(R^{1'})_m(OR^{2'})_{3-m}$ (in formula (a), m, $R^{1'}$, and $R^{2'}$ are the same as in the above formula);

$Z^1$ is a carbon atom or a heteroatom, with the proviso that when $Z^1$ is a heteroatom other than a nitrogen atom, $R^2$ is not substituted, and when $Z^1$ is a nitrogen atom, $R^2$ may be substituted;

$R^a$ and $R^b$ may be the same or different and each is a hydrogen atom, a straight or branched lower alkyl, lower alkoxy, or lower alkyl-carbonyl group that may be substituted with one or more halogen atoms, lower alkenyl, lower alkynyl, carbamoyl, an unsaturated heterocyclic ring, an aromatic ring, nitro, amino, amido, an ester group, carboxyl, hydroxyl, cyano, a halogen atom, or a group represented by formula (a):-Si$(R^{1'})_m(OR^{2'})_{3-m}$ (in formula (a), m, $R^{1'}$, and $R^{2'}$ are the same as in the above formula);

$R^a$ and $R^b$ may be combined to form a bicyclo ring;

p and q are each 1 or 2, p and q are each 2 when W is a double bond, and p and q are each 1 when W is a triple bond;

W is a double bond or a triple bond; and $W^a$ is a single bond or a double bond.

11. The method according to claim 9, comprising:

reacting a compound represented by formula (1b) with a compound represented by formula (2) in the presence of the ruthenium catalyst to obtain a compound represented by formula (3b),

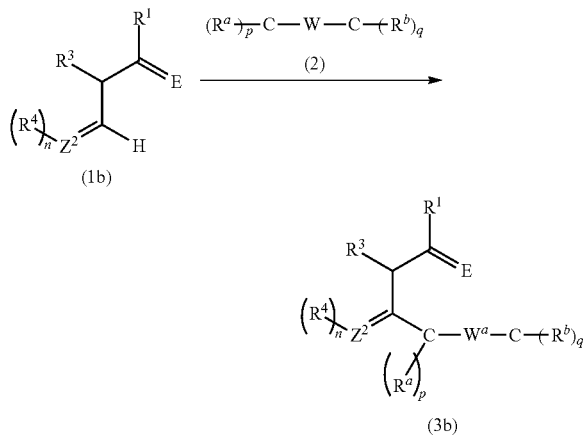

wherein

E is an oxygen atom;

$R^1$ is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-Si$(R^{1'})_m(OR^{2'})_{3-m}$ (in formula (a), m is an integer of 0 to 3, $R^{1'}$ and $R^{2'}$ may be the same or different and each is lower alkyl or an aromatic ring), $R^3$ is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-Si$(R^{1'})_m(OR^{2'})_{3-m}$ (in formula (a), m, $R^{1'}$, and $R^{2'}$ are the same as in the above formula), or $R^1$ and $R^3$ are bonded to each other via or not via one or more heteroatoms to form a 5- to 10-membered saturated hydrocarbon ring, a 5- to 10-membered unsaturated heterocyclic ring, or a 5- to 10-membered aromatic ring, wherein the formed ring may have at least one substituent selected from the group consisting of a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, and a halogen atom;

$R^4$ is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-Si$(R^{1'})_m(OR^{2'})_{3-m}$ (in formula (a), m, $R^{1'}$, and $R^{2'}$ are the same as in the above formula);

$Z^2$ is a carbon atom or a nitrogen atom;

n is 1 or 2, n is 2 and $R^4$s may be the same or different when $Z^2$ is a carbon atom, and n is 1 when $Z^2$ is a nitrogen atom;

$R^a$ and $R^b$ may be the same or different and each is a hydrogen atom, a straight or branched lower alkyl, lower alkoxy, or lower alkyl-carbonyl group that may be substituted with one or more halogen atoms, lower alkenyl, lower alkynyl, carbamoyl, an unsaturated heterocyclic ring, an aromatic ring, nitro, amino, amido, an ester group, carboxyl, hydroxyl, cyano, a halogen atom, or a group represented by formula (a):-Si$(R^{1'})_m(OR^{2'})_{3-m}$ (in formula (a), m, $R^{1'}$, and $R^{2'}$ are the same as in the above formula);

$R^a$ and $R^b$ may be combined to form a bicyclo ring;

p and q are each 1 or 2, p and q are each 2 when W is a double bond, and p and q are each 1 when W is a triple bond;

W is a double bond or a triple bond; and $W^a$ is a single bond or a double bond.

12. The method according to claim 9, comprising:

reacting a compound represented by formula (1c) with a compound represented by formula (2) in the presence of the ruthenium catalyst to obtain a compound represented by formula (3c),

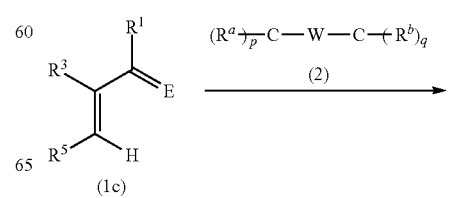

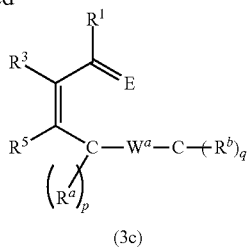

(3c)

wherein
- E is an oxygen atom;
- $R^1$ is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-$Si(R^{1'})_m(OR^{2'})_{3-m}$ (in formula (a), m is an integer of 0 to 3, $R^{1'}$ and $R^{2'}$ may be the same or different and each is lower alkyl or an aromatic ring),
- $R^3$ is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-$Si(R^{1'})_m(OR^{2'})_{3-m}$ (in formula (a), m, $R^{1'}$, and $R^{2'}$ are the same as in the above formula), or
- $R^1$ and $R^3$ are bonded to each other via or not via one or more heteroatoms to form a 5- to 10-membered saturated hydrocarbon ring, a 5- to 10-membered unsaturated heterocyclic ring, or a 5- to 10-membered aromatic ring, wherein the formed ring may have at least one substituent selected from the group consisting of a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, and a halogen atom;
- $R^5$ is a hydrogen atom, a straight or branched lower alkyl, lower alkoxy, or lower alkyl-carbonyl group that may be substituted with one or more halogen atoms; carbamoyl, an unsaturated heterocyclic ring, an aromatic ring, nitro, amino, amido, an ester group, carboxyl, hydroxyl, cyano, a halogen atom, or a group represented by formula (a):-$Si(R^{1'})_m(OR^{2'})_{3-m}$ (in formula (a), m, $R^{1'}$, and $R^{2'}$ are the same as in the above formula);
- $R^a$ and $R^b$ may be the same or different and each is a hydrogen atom, a straight or branched lower alkyl, lower alkoxy, or lower alkyl-carbonyl group that may be substituted with one or more halogen atoms, lower alkenyl, lower alkynyl, carbamoyl, an unsaturated heterocyclic ring, an aromatic ring, nitro, amino, amido, an ester group, carboxyl, hydroxyl, cyano, a halogen atom, or a group represented by formula (a):-$Si(R^{1'})_m(OR^{2'})_{3-m}$ (in formula (a), m, $R^{1'}$, and $R^{2'}$ are the same as in the above formula);
- $R^a$ and $R^b$ may be combined to form a bicyclo ring;
- p and q are each 1 or 2, p and q are each 2 when W is a double bond, and p and q are each 1 when W is a triple bond;
- W is a double bond or a triple bond; and
- $W^a$ is a single bond or a double bond.

* * * * *